US007517542B2

(12) United States Patent
Jeong et al.

(10) Patent No.: US 7,517,542 B2
(45) Date of Patent: Apr. 14, 2009

(54) **ABIETANE DITERPENOID COMPOUND, AND COMPOSITION COMPRISING EXTRACT OF *TORREYA NUCIFERA*, OR ABIETANE DITERPENOID COMPOUNDS OR TERPENOID COMPOUNDS ISOLATED FROM THEM FOR PREVENTION AND TREATMENT OF CARDIOVASCULAR DISEASE**

(75) Inventors: Tae-Sook Jeong, Taejeon-si (KR); Woo-Song Lee, Taejeon-si (KR); Hyoung-Chin Kim, Taejeon-si (KR); Yang-Kyu Choi, Taejeon-si (KR); Ju-Ryoung Kim, Taejeon-si (KR); So-Jin An, Taejeon-si (KR); Kyoung-Ran Im, Taejeon-si (KR); Ki-Chang Jang, Jeju-si (KR); Og-Sung Moon, Taejeon-si (KR); Jun-Seock Son, Taejeon-si (KR)

(73) Assignee: Korea Research Institute of Bioscience, Taijeon-Si (KR)

( * ) Notice: Subject to any disclaimer, the term of this patent is extended or adjusted under 35 U.S.C. 154(b) by 152 days.

(21) Appl. No.: 10/591,282

(22) PCT Filed: Feb. 22, 2005

(86) PCT No.: PCT/KR2005/000472

§ 371 (c)(1),
(2), (4) Date: Aug. 31, 2006

(87) PCT Pub. No.: WO2005/084141

PCT Pub. Date: Sep. 15, 2005

(65) Prior Publication Data

US 2007/0190192 A1     Aug. 16, 2007

(30) Foreign Application Priority Data

Mar. 3, 2004  (KR) .................. 10-2004-0014236
Nov. 4, 2004  (KR) .................. 10-2004-0089372
Dec. 24, 2004 (KR) .................. 10-2004-0112140

(51) Int. Cl.
    *A01N 65/00*  (2006.01)
(52) U.S. Cl. ...................................... 424/770
(58) Field of Classification Search ............... None
    See application file for complete search history.

(56) References Cited

OTHER PUBLICATIONS

Flores et al. (( Extractable conpounds of Native Trees Chemical and Biological Study: Bark of Prumnopytis andina (Podocarpaceae) and Austrocedrus chilensis (Cupressaceae) Bol. Soc. Chil. Quim. vol. 46, No. 1, Mar. 2001, pp. 1-5)).*
Starratt et al. (Rebaudioside F. A diterpene glycoside fro Stevia rebaudiana, Phytochemistry, vol. 59, 2002, pp. 367-370).*

James R. Hanson, (Diterpenoids, Natural. Products. Report., 2004, vol. 21, pp. 312-320).*
Xiang et al, (A New Abietane Diterpenoid from Orthosiphon wulfeniodes, Chinese Chemical Letter vol. 13, 2002, No. 2, pp. 141-142).*
Tada et al, (Synthesis of (+)- and (-)-ferruginol via asymmetric cyclization of a polyene, Journal Chemistry Society, Perkin Trans. vol. 1., 2000, pp. 2657-2664).*
Fukushima et al., Isolation of 6-Hydroxydehydroabietinol and Hinokiol from the Leaves of Torreya nucifera Sieb. et Zucc., Biol. Chem., vol. 32, No. 9, p. 1103-1107, 1968.*
Principles in Biochemistry, LIPID Biosynthesis, pp. 770-817, 3rd Edition, 2000 Worth Publishers, New York.
Daniel Steinberg, et al., Beyond Cholesterol, The New England Journal Medicine, vol. 320, No. 14, pp. 915-924, 1989.
Judith A. Berliner, et al., Atherosclerosis: Basic Mechanisms . . . , Circulation, vol. 91, Np. 9, pp. 2488-2496, 1995.
Peter Wagner, et al., Copper Ions Promote Peroxidation of Low . . . , Arterioscel. Thromb. Vasc. Biol., vol. 17, pp. 3338-3346, 1997.
Masa-aki Kawashiri, et al., High-Density Lipoprotein Metabolism: Molecular . . . , Curr. Atheroscler. Res., vol. 2, pp. 363-372, 2000.
Eva Hurt-Camejo, et al., Phospholipase A2 In Vascular Disease, Circulation Research, vol. 2, pp. 298-304, 2001.
Lawrence L. Rudel, et al., Acyl Coenzyme A: Cholesterol . . . , Curr. Opin. Lipidol., vol. 12, pp. 121-127, 2001.
Kimberly K. Buhman, et al., Resistance to Diet-Induced Hypercholesterolemia . . . , Nature Medicine, vol. 6, No. 12, pp. 1341-1347, 2000.
Tsutomu Sakai, et al., The Structure and Stereochemistry of Four New Sesquiterpenes . . . , Bull. Chem. Soc. Japan, vol. 38, pp. 381-387, 1965.
Yoshikatsu Sayama, et al., New Diterpenes of Torreya . . . , Agric. Bio. Chem., vol. 35, No. 7, pp. 1068-1073, 1971.
Leslie J. Harrison, et al., 18-Oxoferruginol From the Leaf of Torreya Nucifera, Phytochemistry, vol. 26, pp. 1211-1212, 1987.
Iqbal Ahmad, et al., Tetrahydroamentoflavone From Nuts . . . , Phytochemistry, vol. 20, pp. 1169-1170, 1981.
Yueh-Hsiung Kuo, et al., Chemical Constituents of the Pericarp . . . , J. Chin. Chem. Soc., vol. 46, No. 5,, pp. 819-825, 1999.

(Continued)

*Primary Examiner*—Christopher R Tate
*Assistant Examiner*—Deborah A. Davis
(74) *Attorney, Agent, or Firm*—Lucas & Mercanti, LLP

(57) ABSTRACT

The present invention relates to a composition for the prevention and the treatment of cardiovascular disease containing extracts of *T. nucifera* or abietane diterpenoid compound or terpenoid compound isolated from the same as an effective ingredient.

*T. nucifera* extracts or abietane diterpenoid compound or terpenoid compound isolated from the same of the present invention not only shows excellent anti-oxidative activity to LDL but also effectively inhibits ACAT activity. Further, *T. nucifera* extracts of the present invention reduce blood LDL cholesterol and total cholesterol.

Therefore, the composition of the present invention can be effectively used for the prevention and the treatment of cardiovascular diseases including hyperlipidemia and atherosclerosis caused by the LDL oxidation and the synthesis and accumulation of cholesteryl ester.

4 Claims, No Drawings

OTHER PUBLICATIONS

Hanne L. Ziegler, et al., Possible Artefacts in the in Vitro . . . , Planta Med., vol. 68, pp. 547-549, 2002.

Kiyoko Takamura, The Enhanced Effect of Anthracene on the Polarographic . . . , Bull. Chem. Soc. Jpn., vol. 36, pp. 1053-1054.

Byung-Tae Ahn, et al., Low-Density Lipoprotein-Antioxidant . . . , J. Nat. Prod., vol. 64, pp. 1562-1564, 2001.

Evan A. Stein, et al., Development and Evaluation of a Method for Quantitation . . . , Clin. Chem., vol. 24, pp. 1112-1115, 1978.

Paul R. Finley, et al., Cholesterol in High-Density Lipoprotein: Use . . . , Clin. Chem., vol. 24, pp. 931-933, 1978.

G. R. Warnick, et al., Dextran Sulfate-Mg2+ Precipitation Procedure . . . , Clin. Chem., vol. 28, pp. 1379-1388, 1982.

\* cited by examiner

ABIETANE DITERPENOID COMPOUND, AND COMPOSITION COMPRISING EXTRACT OF *TORREYA NUCIFERA*, OR ABIETANE DITERPENOID COMPOUNDS OR TERPENOID COMPOUNDS ISOLATED FROM THEM FOR PREVENTION AND TREATMENT OF CARDIOVASCULAR DISEASE

This patent application claims the benefit of priority from Korean Patent Application No. 10-2004-0014236 filed Mar. 3, 2004, Korean Patent Application No. 10-2004-0089372, filed on Nov. 4, 2004 and Korean Patent Application No. 10-2004-0112140, filed on Dec. 24, 2004 through PCT Application Ser. No. PCT/KR2005/000472 filed Feb. 22, 2005, the contents of each of which are incorporated herein by reference.

TECHNICAL FIELD

The present invention relates to a novel abietane diterpenoid compound and a composition for the prevention and the treatment of cardiovascular disease containing extracts of *Torreya nucifera* or abietane diterpenoid compounds or terpenoid compounds isolated from the same as an effective ingredient.

BACKGROUND ART

Cardiovascular diseases including atherosclerosis increase gradually as adult disease is growing. Atherosclerosis frequently occurs in cerebral artery or in coronary artery. Cerebral atherosclerosis carries headache, dizziness and mental disorder, and is a cause of cerebral infraction. Coronary arteriosclerosis causes pain and arrhythmia in the heart, leading to angina pectoris or myocardial infraction. Such diseases further cause hypertension, heart disease, cerebral hemorrhage, etc, making atherosclerosis related diseases the leading cause of death of men at the age of 50~60 s.

High blood cholesterol causes coronary cardiovascular diseases. In order to reduce blood cholesterol, inhibition of enzyme involved in lipid metabolism or a dietary treatment designed to limit the intake of cholesterol and lipid has to be enforced.

For the purpose of preventing such diseases, attempts have been made to reduce low-density lipoprotein (LDL) by inhibiting cholesterol absorption and biosynthesis thereof (Principles in Biochemistry, lipid biosynthesis, 770-817, 3rd Edition, 2000 Worth Publishers, New York; Steinberg, D. et al. *N. Engl. J. Med.*, 320: 915-924, 1989).

The production of LDL oxide in blood has been the subject of study since it is regarded as the cause of atherosclerosis (*Circulation*, 91: 2488-2496, 1995; *Arterioscler. Thromb. Vasc. Biol.*, 17: 3338-3346, 1997). In particular, a recent report saying that the production of foam cells is resulted from the inflow of HM-LDL (highly modified LDL), generated by peroxidation and structural transformation of LDL, into macrophages triggered the study on the mechanism of the production and elimination of LDL peroxide (*Curr. Atheroscler. Res.*, 2: 363-372, 2000).

Plague formation and breakage in inside of vascular wall lead to myocardial infraction, and chronic inflammation on vascular wall by the damage of it results in atherosclerosis, which is believed to be a rather defense mechanism than damage mechanism (*Circ. Res.* 89: 298-304, 2001).

Acyl-CoA: cholesterol acyltransferase (ACAT) is an enzyme that esterifies cholesterol and its working mechanism is in act in three regions of body (intestine, liver and vascular wall cells).

First, ACAT esterifies cholesterol and then helps the absorption of cholesterol in intestines. Second, cholesterol which is taken in from outside or produced in inside of body is accumulated in a carrier named VLDL (very low-density lipoprotein) in the liver, which is then provided to each organ of body through blood vessels. At this time, cholesterol is converted into cholesteryl ester by ACAT, enabling the accumulation of cholesterol in a carrier. Third, ACAT esterifies cholesterol in arterial wall cells, promoting the accumulation of cholesterol in cells, which is a direct reason for atherosclerosis.

By the activity of ACAT, foam cells include a huge number of cholesterol ester that is induced from cholesterol. Thus, the formation of foam cells induced from macrophages and smooth muscle cells is very important in experimental and clinical aspects. The growth of foam cells in vascular wall is directly related to the increase of ACAT activity. Therefore, an ACAT inhibitor might be effectively used as a powerful anti-atherosclerotic agent.

Therefore, an ACAT activity inhibitor has to and is expected to (1) reduce cholesterol taken in by inhibiting the absorption of cholesterol in intestines, (2) reduce blood cholesterol by inhibiting the release of cholesterol into blood vessels and (3) prevent atherosclerosis by inhibiting the accumulation of cholesterol in vascular wall cells.

All the ACAT activity inhibitors reported as of today are the inhibitors of the activity of mouse liver microsomal ACAT or mouse liver macrophage (J774) ACAT. Human ACAT is divided into two types; ACAT-1 and ACAT-2. Human ACAT-1 (50 kDa) works largely in the liver, adrenal gland, macrophage and kidney of an adult, and human ACAT-2 (46 kDa) works in the small intestine (Rudel, L. L. et al., *Curr. Opin. Lipidol.* 12: 121-127, 2001). The inhibition of ACAT activity has been a useful strategy for the prevention and the treatment of hypercholesterolemia, cholesterol gallstones or atherosclerosis owing to its mechanisms of inhibiting the absorption of cholesterol taken in from food and inhibiting the accumulation of cholesteryl ester in vascular wall (Buhman, K. K. et al., *Nature Med.* 6: 1341-1347, 2000).

Probucol, N,N'-diphenylenediamine, BHA (butylatedhydroxyanisol) and BHT (butylated hydroxy toluene), synthetic phenols used as anti-oxidatant agents, that have been used for the treatment of hyperlipidemia, reduce LDL cholesterol, weaken LDL-oxidation and reduce the lesion formation, showing excellent anti-oxidative activity but carrying serious side effects, so that they are limited in use.

Therefore, the treatment of patients with hyperlipidemia or atherosclerosis with a LDL anti-oxidative agent together with a lipid lowering agent is promising.

In the meantime, *T. nucifera* is a kind of evergreen needle-leaf tall tree belonging to Taxaceae, which is only distributed in Korea and Japan. *T. nucifera* is an edible, ornamental, medicinal and industrial plant. Its seeds have been eaten or produced as oil. And, its fruits have been used for the treatment of extermination, hair-regrowth, stomach-strengthening, and intestinal hemorrhage, especially in Chineses medicine and folk remedies, and the wood itself has been used for construction, making facilities and making ship (Kim, T. J., Plant Resources in Korea I, p40, Seoul National Univ. Press, 1996; Yook, C.-S., Illustrated of Flora of Asia, p23, Kyungwon Publishing Company, 1997). Ingredients of *T. nucifera*, separated from its leaves and seeds, are sesquiterpenoids (Sakai, T. et al., *Bull. Chem. Soc. Japan*, 38: 381, 1965), labdanes, abietanes including diterpenoids (Sayama, Y. et al, *Agric. Bio. Chem.*, 35: 1068, 1971; Harrison, L. and Asakawa, Y., *Phytochemistry*, 26: 1211, 1987) and flavonoids (Kariyone, T., et al., 78: 1010, 1958), etc.

The present inventors have searched a novel therapeutic agent for hyperlipidemia and atherosclerosis with less side effects, from natural resources. And the present inventors have completed this invention by confirming that *T. nucifera* extracts or abietane diterpenoid compounds or terpenoid compounds isolated from the same has excellent anti-oxidative activity to LDL and inhibiting activity to ACAT enzyme as well.

[Disclosure]

[Technical Problem]

It is an object of the present invention to provide a novel abietane diterpenoid compound.

It is another object of the present invention to provide a composition for the prevention and the treatment of cardiovascular disease containing extracts of *T. nucifera* or abietane diterpenoid compounds or terpenoid compounds isolated from the same as an effective ingredient.

[Best Mode]

The present invention provides a novel abietane diterpenoid compound and a composition for the prevention and the treatment of cardiovascular disease containing extracts of *T. nucifera* or abietane diterpenoid compounds or terpenoid compounds isolated from the same as an effective ingredient.

The composition of the present invention includes pharmaceutical compositions, which are effective for the prevention and the treatment of cardiovascular disease, and for health food compositions.

Hereinafter, the present invention is described in detail.

The present invention provides a novel abietane diterpenoid compound represented by the following formula 1.

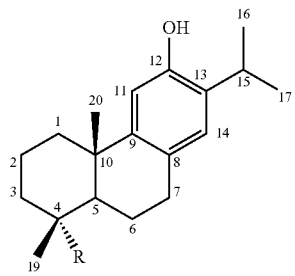

[Formula 1]

(R is dimetoxymethyl.)

The abietane diterpenoid compound of formula 1 is 12-hydroxyabietic-8,11,13-trien-18-dimethylacetyl.

The present invention also provides a composition for the prevention and the treatment of cardiovascular disease comprising either *T. nucifera* extracts or abietane diterpenoid compounds represented by the following formula 1 that are isolated from the extracts or terpenoid compounds selected from a group consisting of compounds represented by the following formula 2~formula 5 that is also isolated from the extracts, as an effective ingredient.

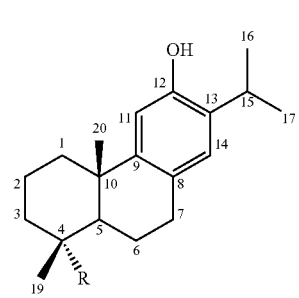

<Formula 1>

(R is methyl, hydroxymethyl, aldehyde, methylester methoxymethyl.)

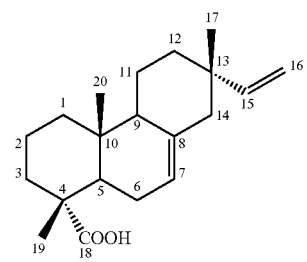

[Formula 2]

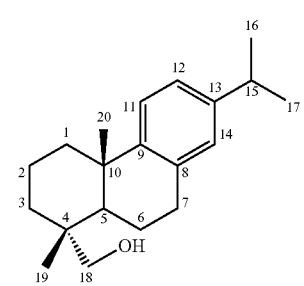

[Formula 3]

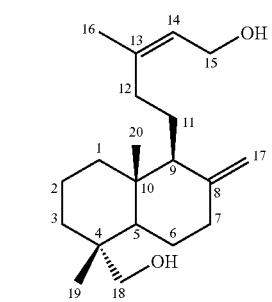

[Formula 4]

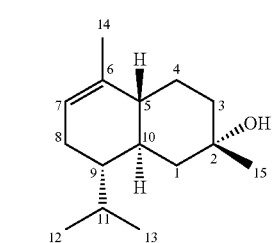

[Formula 5]

Abietane diterpenoid compounds of the formula 1 include ferruginol (R=methyl), 18-hydroxyferruginol (R=hydroxymethyl), 18-oxoferruginol (R=aldehyde) and 12-hydroxyabietic-8,11,13-trien-18-oic acid methyl ester (R=methyl ester). The compounds of formula 2 and formula 3 are isopimaric acid and dehydroabietinol, respectively, both are abietane diterpenoid compounds, and the compound of formula 4 is kayadiol, a labdane diterpenoid compound. The compound of formula 5 is δ-cadinol, a sesquiterpenoid compound.

The compounds of formula 1~formula 5 can be used in the form of pharmaceutically acceptable salts, in which all the salts, hydrates and solvates that can be prepared by the conventional method are included.

*T. nucifera* extracts of the present invention are extracted from leaves, stems or seeds of *T. nucifera* by using water, alcohol or the mixture thereof. At this time, alcohol is preferably selected from a group consisting of methanol, ethanol and butanol.

Abietane diterpenoid compounds or terpenoid compounds are isolated from *T. nucifera* extracts by the conventional method, and reagents on the market can be used.

The extraction, separation and purification methods of *T. nucifera* extracts or abietane diterpenoid compounds or terpenoid compounds separated from the extracts are described hereinafter.

Dried *T. nucifera* leaves (stems or seeds) are dipped in water, which are heated at 40~120° C. for 2~24 hours. The solution is filtered to obtain extracts and solid residues. The obtained extracts are concentrated under reduced pressure to give hot water extracts of *T. nucifera* leaves (stems or seeds).

Or, dried *T. nucifera* leaves (stems or seeds) are dipped in methanol (or ethanol) for 3 weeks and then the solution is filtered. Charcoal is added to the filtrate, followed by stirring at room temperature for 12 hours. The solution is filtered again and then concentrated, to which water is added to suspend the solution. The solution is then filtered once again. The obtained upper layer is dissolved in ethyl acetate, which is then concentrated, resulting in oily yellow substances. The concentrated solution is dissolved in dichloromethane, to which n-hexane is slowly added in order to perform recrystallization. The solution is filtered with a filter-glass. The resultant liquid is concentrated, resulting in oily substances.

The prepared oil fraction was examined to measure its anti-oxidative activity to LDL and inhibiting effects on human ACAT-1 and -2, resulting in the confirmation that the oil fraction has dual inhibiting effect against LDL-oxidation and ACAT.

The obtained ethyl acetate oil fraction is separated by silica-gel column chromatography by using the mixed solvents of n-hexane and ethyl acetate as the mobile phases. At this time, the oil fraction is separated into 17 fractions (fraction 1~17) by using the mixed solvents of n-hexane and ethyl acetate as mobile phase solvents, and at this time, the mixing ratios of n-hexane and ethyl acetate (EtOAc) are 98:2, 97:3, 95:5, 10:1, 5:1, 3:1, 1:1 and EtOAc 100% (v/v).

Fraction 8 (593 mg) that shows the best anti-oxidative activity is separated by silica-gel column chromatography by using the mixed solvents of n-hexane and ethyl acetate as mobile phases. At this time, as the mobile phase solvents, n-hexane is mixed with EtOAc at the ratios of 98:2, 95:5, 10:1, 5:1, 3:1, 1:1 and EtOAc 100% (v/v), resulting in 11 fractions (fraction 8~8-17). Among 11 fractions, fraction 8-8~8-10 (n-hexane:EtOAc=5:1~1:1, 149 mg), that show the high anti-oxidative activities, are mixed, and the mixture is purified by preparative TLC ($CHCl_3$/MeOH=80:1) and sephadex LH-20 column ($CHCl_3$/MeOH=1:1) to give two purified compounds. These compounds are 12-hydroxyabietic-8,11,13-trien-18-dimethylacetal (R=dimetoxymethyl, 18 mg) and 12-hydroxyabietic-8,11,13-trien-18-oic acid methylester (R=methylester, 17.5 mg) of formula 1.

Ethyl acetate oil fraction obtained above is separated by silica-gel column chromatography by using the mixed solvents of n-hexane and ethyl acetate as the mobile phases. At this time, the mobile phase solvents are preferably ethyl acetate:n-hexane=10~20:90~80 (v/v). Among compounds of formula 1, which are pure active ingredients, ferruginol (R=methyl, 22 mg), 18-hydroxyferruginol (R=hydroxymethyl, 307 mg) and 18-oxoferruginol (R=aldehyde, 62 mg) are obtained from 1 kg of dried *T. nucifera* leaves by the above method.

Ethyl acetate oil fraction obtained above is separated by silica-gel column chromatography by using the mixed solvents of ethyl acetate and n-hexane as the mobile phases. The mobile phase solvents are prepared by mixing n-hexane and ethyl acetate at the ratio of 10:1, 5:1, 3:1, 1:1 (v/v) and EtOAc 100%, resulting in the separation of 11 fractions (fraction 1~11).

Fraction 5 showing a very strong ACAT inhibiting activity is separated by silica-gel column chromatography by using the mixed solvent of n-hexane and ethyl acetate as a mobile phase. At this time, the mobile phase solvent is prepared as n-hexane:ethyl acetate=7:1 (v/v) to separate 7 fractions (fraction 5-1~5-7) from fraction 5. Fraction 5-4 having excellent ACAT inhibiting activity is separated by silica-gel column chromatography. And, 4 fractions (fraction 5-4-1~5-4-4) are separated therefrom by using chloroform 100% as a mobile phase. From the fraction 5-4-1, the compound of formula 2 (isopimaric acid, 76 mg), a pure active compound, is separated.

14 fractions (fraction 10-1~10-14) are separated from fraction 10, prepared from the first column, by silica-gel column chromatography using methylene chloride:methanol=50:1 (v/v) as a mobile phase solvent. And, 11 fractions (fraction 10-4-1~10-4-11) are separated from the active fraction 10-4 by C18 reversed phase column chromatography using methanol:water=15:1 as a mobile phase solvent. 5 fractions (10-4-5-1~10-4-5-5) are separated from the fraction 10-4-5 having strong ACAT inhibiting activity by silica-gel column chromatography using the mixed solvents of n-hexane and ethyl acetate which are prepared at the ratios of 50:1, 30:1, 10:1, 1:1 (v/v) and EtOAc 100% as the mobile phase solvents. A pure active compound represented by formula 3 (dehydroabietinol, 25 mg) is obtained from the fraction 10-4-5-2.

A pure active compound of formula 4 (kayadiol, 40 mg) is given from the fraction 11 obtained from the first column by using recrystallization solvent n-hexane:ethyl acetate=5:1 (v/v).

12 fractions (fraction 10-6-1~10-6-12) are separated from fraction 10-6, one of active fraction among 14 fractions obtained from the second column, by C18 reversed phase column chromatography using methanol:water=10:1 (v/v) as a mobile phase solvent. Silica-gel column chromatography is also performed with active fraction 10-6-3 using n-hexane:ethyl acetate=15:1, 10:1, 5:1, 1:1 and EtOAc 100% as the mobile phase solvents, resulting in 5 fractions (fraction 10-6-3-1~10-6-3-5). Finally, a pure active compound of formula 5 (δ-cadinol, 15 mg) is prepared from the fraction 10-6-3-1.

*T. nucifera* extracts of the present invention or abietane diterpenoid compound isolated from the same has low $IC_{50}$ value, indicating that it has excellent anti-oxidative activity to LDL.

*T. nucifera* extracts of the present invention or abietane diterpenoid compound or terpenoid compound isolated from the same show excellent ACAT inhibiting activity in hACAT-1 and in hACAT-2.

*T. nucifera* extracts of the present invention also reduce serum LDL and blood cholesterol.

Therefore, the composition of the present invention can be effectively used for the prevention and the treatment of cardiovascular diseases such as hyperlipidemia and atherosclerosis which are caused by the synthesis and the accumulation of cholesteryl ester.

The composition of the present invention can additionally include, in addition to *T. nucifera* extracts or abietane diterpenoid compound or terpenoid compound isolated from the same, one or more effective ingredients having same or similar function to the extract or compounds separated therefrom.

The composition of the present invention can also include, in addition to the above-mentioned effective ingredients, one or more pharmaceutically acceptable carriers for the administration. Pharmaceutically acceptable carriers can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each diseases or according to ingredients by following the method represented in Remington's Pharmaceutical Science (the newest edition), Mack Publishing Company, Easton PA.

The composition of the present invention can be administered orally or parenterally (for example, intravenous, hypodermic, local or peritoneal injection). The effective dosage of the composition can be determined according to weight, age, gender, health condition, diet, administration frequency, administration method, excretion and severity of a disease. The dosage of *T. nucifera* extracts is 10~2,000 mg/kg per day, and preferably 50~500 mg/kg per day. The dosage of the compounds of formula 1~formula 5 is 0.1~100 mg/kg per day and preferably 0.5~10 mg/kg per day. Administration frequency is once a day or preferably a few times a day.

*T. nucifera* extracts of the present invention or abietane diterpenoid compound or terpenoid compound isolated from the same was orally administered to mice to investigate toxicity. As a result, it was evaluated to be safe substance since its estimated $LD_{50}$ value is much greater than 1,000 mg/kg in mice.

The composition of the present invention can be administered singly or treated along with surgical operation, hormone therapy, chemotherapy and biological reaction regulator, to prevent and treat cardiovascular diseases.

The composition of the present invention can be included in health foods for the purpose of improving cardiovascular diseases. At this time, *T. nucifera* extracts of the present invention or abietane diterpenoid compound or terpenoid compound isolated from the same can be added as it is or after being mixed with other food or ingredients, according to the conventional method. The mixing ratio of effective ingredients is determined by the purpose of use (prevention, health or therapeutic treatment). In the case of producing food or beverages containing *T. nucifera* extracts of the present invention or abietane diterpenoid compound or terpenoid compound isolated from the same, it is preferably added by 1~20 weight %, more preferably 5~10 weight %, to the raw material. However, the content of the extract might be less than the above when it is administered for long-term to improve health conditions but the effective dosage could contain more than the above amount because the extract of the invention is very safe.

There is no limit in applicable food, which is exemplified by meat, sausages, bread, chocolate, candies, snacks, cookies, pizza, ramyun, noodles, dairy products including ice cream, soups, beverages, tea, drinks, alcoholic drinks and vitamin complex, etc, and in fact every health food generally produced are all included.

Health beverages containing the composition of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xylitol, sorbitol and erythritol. As a sweetener, either natural sweetener such as thaumatin and stevia extract or artificial sweetener such as saccharin and aspartame can be used. The ratio of natural carbohydrate to the composition of the present invention is preferably 0.01~0.04 g to 100 ml, more preferably 0.02~0.03 g to 100 ml.

In addition to the ingredients mentioned above, the composition of the present invention can include in variety of nutrients, vitamines, electrolytes, flavoring agents, colouring agents, pectic acid and its salts, arginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and fruit flesh addable to vegetable beverages. All the mentioned ingredients can be added singly or together. The mixing ratio of those ingredients does not matter in fact, but in general, each can be added by 0.01~0.1 weight part per 100 weight part of the composition of the invention.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Extraction, Isolation and Purification of Abietane Diterpenoid Compound from *T. nucifera*

1. Preparation of Hot Water Extracts from *T. nucifera* Leaves 1 kg of *T. nucifera* leaves purchased in Jeju island, Korea, was washed and dried. 1000 ml of water was added to 250 g of the dried *T. nucifera* leaves, which was boiled at 90° C. for 4 hours. The solution was filtered, resulting in extracts and solid phase residues. The obtained extracts were concentrated under reduced pressure to give 30 g of hot water extracts of *T. nucifera* leaves.

2. Preparation of Hot Water Extracts from *T. nucifera* Seeds

Hard shells of *T. nucifera* seeds were removed and then the seeds were pulverized by using a pulverizer. 500 ml of water was added to 120 g of crushed *T. nucifera* seeds, which was boiled at 90° C. for 4 hours. The solution was filtered, resulting in extracts and solid phase residues. The obtained extracts were concentrated under reduced pressure to give 9 g of hot water extracts of *T. nucifera* seeds.

3. Preparation of Alcohol Extracts from *T. nucifera* Leaves 2.16 kg of *T. nucifera* leaves purchased in Jeju island, Korea, was washed and dried. The dried *T. nucifera* leaves were put in 18 l of 100% ethanol, which was left at room temperature for 3 weeks. The solution was filtered with a filter paper. Charcoal was added to the filtrates, followed by stirring at room temperature for 12 hours. The solution was filtered and concentrated under reduced pressure to give an oily yellow subject.

4. Isolation and Purification of Abietane Diterpenoid Compounds from *T. nucifera* Extracts The oily yellow subject obtained from the above 3 was suspended in 1,000 ml of water, then fractionized with n-hexane, chloroform and ethyl acetate in that order. As a result, 75 g of n-hexane soluble extracts, 37 g of chloroform soluble extracts and 18 g of ethyl acetate soluble extracts were obtained. The oily yellow subject obtained from the ethyl acetate layer has excellent anti-oxidative effect on LDL.

Silica-gel column chromatography (silica-gel: Merck, Art. 9385, column size: φ7×40 cm) was performed with 18 g of ethyl acetate oil fraction obtained above by using the mixed solvents of n-hexane and ethyl acetate as the mobile phases. At this time, the mixed solvents used as mobile phases was developed by 15 l respectively as n-hexane:EtOAc=98:2, 97:3, 95:5, 10:1, 5:1, 3:1, 1:1 and EtOAc 100% (v/v) to separate 17 fractions (fraction 1~17), and anti-oxidative activity of each fraction was investigated.

Fraction 8 (593 mg) that showed the best anti-oxidative activity was separated by silica-gel column chromatography by using the mixed solvents of n-hexane and ethyl acetate as mobile phases. At this time, the mobile phase solvents were developed as n-hexane:EtOAc=98.2, 95:5, 10:1, 5:1, 3:1, 1:1 and EtOAc 100% (v/v), by 100 ml each, resulting in 11 fractions (fraction 8-1~8-17). Anti-oxidative activity of each fraction was investigated. And the mixture of fractions 8-8~8-10 (n-hexane:EtOAc=5:1~1:1, 149 mg), each of which had the most excellent anti-oxidative activity, was purified by preparative TLC (Silica-gel 60F$_{254}$, Merck, Art. 5744, CHCl$_3$/MeOH=80:1) and sephadex LH-20 column chromatography(Sigma-Aldrich Co., USA, CHCl$_3$/MeOH=1:1), resulting in two purified compounds, that were two of those compounds represented by formula 1 (18 mg, 17.5 mg).

5. Analyses of the Structures of Abietane Diterpenoid Compounds

The molecular weight and formula of the compound obtained in the above 4 were investigated by using VG high resolution GC/MS spectrometer (Election Ionization MS, Autospec-Ultima), and polarity of it was also measured with a polarimeter (Jasco DIP-181 digital polarimeter). The NMR analyses were performed (Bruker AMX 300, 500) to obtain $^1$H NMR, $^{13}$C NMR, HOMO-COSY, HMQC ($^1$H-Detected heteronuclear Multiple-Quantum Coherence), HMBC (Heteronuclear Multiple-Bond Coherence) and DEPT (Distortionless Enhancement by Polarization) spectra and molecular structure of the compound was determined.

The results are shown in below. After comparing with the other results shown in earlier reports, one of the compounds represented by formula 1 was confirmed to be 12-hydroxyabietic-8,11,13-trien-18-dimethylacetal, which is a novel compound not reported yet. The other compound was confirmed to be 12-hydroxyabietic-8,11,13-trien-18-oic acid methylester (*Chem. Nat. Compd.* (*Engl. Transl*), 24: 447, 1988).

12-hydroxyabietic-8,11,13-trien-18-dimethylacetal

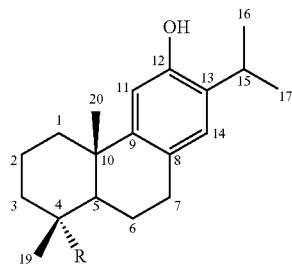

(R is dimethoxymethyl.)
1) Physical property: yellow oil
2) Polarity: $[\alpha]_D^{25}$ −5.8° (c=0.3, CHCl$_3$)
3) Molecular weight: 346
4) Molecular formula: C$_{22}$H$_{34}$O$_3$
5) $^1$H NMR (CDCl$_3$, 500 MHz) δ 0.9 (s, 3H, H-19), 1.12 (s, 3H, H-20), 1.15 (d, J=7.2 Hz, H-16), 1.16 (d, J=7.2 Hz, H-17), 1.27 (dt, J=4.2, 12.7 Hz, H-1a), 1.36-1.43 (m, 2H, H-3), 1.53-1.62 (m, 2H, H-2), 1.64-1.75 (m, 2H, H-6), 1.81 (dd, J=1.7, 12.1 Hz, H-5), 2.05 (d like, J=12.6 Hz, H-1b), 6.55 (s, 1H, H-11), 6.75 (s, 1H, H-14).
6) $^{13}$C NMR (CDCl$_3$, 125 MHz) δ 16.7 (C-19), 18.3 (C-2), 19.4 (C-6), 22.5 (C-16), 22.7 (C-17), 25.2 (C-20), 26.7 (C-15), 29.3 (C-7), 30.4 (C-3), 37.3 (C-10), 38.2 (C-1), 42.6 (C-4), 42.8 (C-5), 58.7 (C-18b), 59.0 (C-18a), 110.9 (C-11), 113.3 (C-18), 126.5 (C-14), 126.9 (C-8), 131.4 (C-13), 148.7 (C-9), 150.7 (C-12).
7) EIMS (rel. int.) m/z [M]$^+$ 59 (22%), 75 (100%), 189 (14%), 201 (10%), 346 (33%).

12-hydroxyabietic-8,11,13-trien-18-oic acid methylester

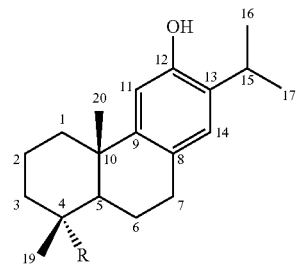

(R is methylester.)
1) Physical property: yellow oil
2) Polarity: $[\alpha]_D^{25}$ +75.7° (c=0.28, EtOH)
3) Molecular weight: 330
4) Molecular formula: C$_{21}$H$_{30}$O$_3$
5) $^1$H NMR (CDCl$_3$, 500 MHz) δ 1.12 (s, 3H, H-20), 1.15 (d, J=7.4 Hz, 3H, H-16), 1.16 (d, J=7.3 Hz, 3H, H-17), 1.19 (s, 3H, H-19), 1.29 (m, 1H, H-6α), 1.41 (m, 1H, H-2α), 1.55-1.77 (m, 5H, H-1α, H-2β, H-3, H-6β), 2.12 (d like, J=12.7 Hz, 1H, H-1β), 2.14 (dd, J=1.7, 12.5 Hz, 1H, H-5), 2.74 (m, 2H, H-7), 3.04 (m, 1H, H-15), 3.59 (s, 3H, CO$_2$Me), 4.58 (s, —OH), 6.55 (s, 1H, H-11), 6.74 (s, 1H, H-14).
6) $^{13}$C NMR (CDCl$_3$, 125 MHz) δ 16.5 (C-19), 18.5 (C-2), 21.8 (C-6), 22.5 (C-16), 22.7 (C-17), 25.0 (C-20), 26.8 (C-15), 29.2 (C-7), 36.6 (C-1), 36.9 (C-4), 38.0 (C-3), 44.8 (C-5), 47.7 (C-10), 51.9 (-OMe), 110.8 (C-11), 126.7 (C-14), 127.0 (C-8), 131.7 (C-13), 147.9 (C-9), 150.8 (C-12), 179.2 (C-18)

EXAMPLE 2

Extraction, Isolation and Purification of Abietane Diterpenoid Compounds from *T. nucifera*

1. Preparation of Alcohol Extracts from *T. nucifera* Leaves 1 kg of *T. nucifera* leaves purchased in Jeju island, Korea, was washed and dried. The dried *T. nucifera* leaves were put in 4 l of 95% methanol, which was left at room temperature for 3 weeks. The solution was filtered with a filter paper. Charcoal was added to the filtrates, followed by stirring at room temperature for 12 hours. The solution was filtered and concentrated under reduced pressure to give an oily yellow subject.

2. Isolation and Purification of Abietane Diterpenoid Compounds from *T. nucifera* Extracts The oily yellow substances obtained in the above 1 was suspended in 200 ml of water, which was then filtered with a filter paper. The upper layer was dissolved in ethyl acetate. The solution was concentrated to give 40 g of oily yellow subject. The concentrated solution was dissolved in dichloromethane, to which n-hexane was slowly added, resulting in recrystalization. After filtering with a filter-glass, the liquid phase was concentrated to give 30 g of oily subject.

Anti-oxidative activity to LDL and human ACAT-1 and -2 inhibiting capacity of the obtained oily fraction were investigated, resulting in the confirmation of dual inhibiting effects.

Silica-gel column chromatography (silica-gel: Merck, Art. 9385, column size: ϕ7×40 cm) was performed with 30 g of the oily fraction, obtained above, by using the mixed solvent of n-hexane and ethyl acetate as a mobile phase to separate fractions therefrom. When ethyl acetate:n-hexane=1:9 (v/v) was used as a mobile phase solvent, an active substance was separated best, from which pure active ingredients ferruginol (R=methyl, 22 mg), 18-hydroxyferruginol (R=hydroxymethyl, 307 mg) and 18-oxoferruginol (R=aldehyde, 62 mg) were obtained.

100 mg of 18-hydroxyferruginol (R=hydroxymethyl), a colorless solid compound, was dissolved in 5 ml of dichloromethane, to which 10 ml of n-hexane was slowly added. To the solution was added 1 ml of diethylether, which was left at room temperature for 24 hours. The resultant single crystal was identified by X-ray spectroscopy.

3. Analyses of the Structures of Abietane Diterpenoid Compounds

The results of analyses of the structures of the products obtained in the above 2 are shown in below, that is, the compounds of formula 2 were confirmed to be ferruginol (R=methyl), 18-hydroxyferruginol (R=hydroxymethyl) and 18-oxoferruginol (R=aldehyde) [L. J. Harrison and Y. Asakawa, *Pytochemistry*, 1987, 26, 1211].

[ferruginol]

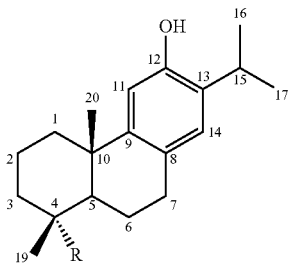

(R is methyl.)
1) Physical property: coloress oil
2) Polarity: $[\alpha]_D^{25}$ +56.6°0 (c=0.6, CHCl$_3$)
3) Molecular weight: 286
4) Molecular formula: $C_{20}H_{30}O$
5) $^1$H-NMR(CDCl$_3$, 300 MHz) δ 0.90(s, 3H, H-18), 0.93(s, 3H, H-19), 1.16 (s, 3H, H-20), 1.21(d, J=5.1 Hz, 3H, H-16), 1.23(d, J=5.1 Hz, 3H, H-17), 1.20(dd, J=3.0, 10.4 Hz, 1H), 1.22(t like, J=5.1 Hz, 6H, H-18, 19), 1.31 (dd, J=1.7, 9.3 Hz, 1H), 1.38(dd, J=2.8, 10.4 Hz, 1H), 1.58-1.89(m, 3H), 1.84(m, 1H), 2.15(dd like, J=0.7, 8.7 Hz, 1H), 2.76(ddd, J=1.3, 5.3, 8.5 Hz, 1H, H-7a), 2.85(ddd, J=1.3, 5.2, 8.6 Hz, 1H, H-7b), 3.10(m, 1H, H-15), 4.49(br, 1H, —OH), 6.62(s, 1H, H-13), 6.82(s, 1H, H-10).

6) $^{13}$C-NMR(CDCl$_3$, 75 MHz) δ 19.2(C-2), 19.3(C-6), 21.6(C-19), 22.5(C-16), 22.7(C-17), 24.8(C-20), 26.8(C-15), 29.7(C-7), 33.3(C-18), 33.4(C-4), 37.5(C-10), 38.8(C-1), 41.7(C-3), 50.3(C-5), 110.9(C-11), 126.6(C-14), 127.3(C-8), 131.3(C-13), 148.7(C-9), 150.6(C-12).
7) EIMS(rel. int.) m/z [M]+ 69(78.4), (64.5), 159.1(47.5), 175.1(90.7), 187.1(63.8), 201.1(86.0), 215.1(54.4), 229.2(56.5), 271.2(100), 286.2 (99.6).

[18-hydroxyferruginol]

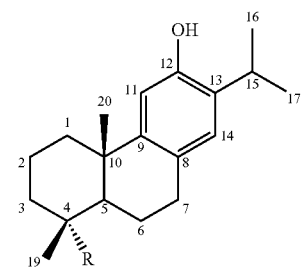

(R is hydroxymethyl.)
1) Physical property: coloress prizm, M.P.=185~187° C.
2) Polarity: $[\alpha]_D^{25}$+110° $^{(c=0.2, CHCl_3)}$
3) Molecular weight: 302
4) Molecular formula: $C_{20}H_{30}O_2$
5) $^1$H-NMR(MeOD, 500 MHz) δ 0.84(s, 3H, H-19), 1.16(t like, J=5.7 Hz, 6H, H-16, 17), 1.18(s, 3H, H-20), 1.31(m, 2H, H-3), 1.51(dt, J=3.9, 13.4 Hz, 1H, H-2a), 1.65(m, 3H, H-6, H-2b), 1.79(m, 2H, H-1), 2.20(d like, J=12.7 Hz, 1H, H-5), 2.75(d like, J=7.7 Hz, 2H, H-7), 3.09(d, J=11.0 Hz, 1H, H-18a), 3.22(m, 1H, H-15), 3.30(s, 1H, ~OH), 3.41(d, J=11.0 Hz, 1H, H-18b), 6.63(s, 1H, H-11), 6.78(s, 1H, H-14).
6) $^{13}$C-NMR(MeOD, 125 MHz) δ 18.0(C-19), 19.8(C-2), 20.1(C-6), 23.2(C-16, 17), 25.8(C-20), 27.7(C-15), 30.4(C-7), 36.3(C-3), 38.4(C-4), 38.9(C-10), 39.9(C-1), 45.0(C-5), 72.0(C-18), 111.6(C-11), 126.9(C-14), 127.2(C-8), 133.2(C-13), 149.1(C-9), 153.1(C-12).
7) EIMS(rel. int.) m/z [M]+ 147(46.5), 175(70.2), 189 (78.0), 201(45.0), 227(50.7), 269(100.0), 287(60.0), 302(95.1).

[18-oxoferruginol]

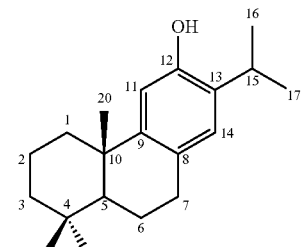

(R is aldehyde.)
1) Physical property: coloress prizm, M.P.=140~142° C.
2) Polarity: $[\alpha]_D^{25}$ +61° (c=0.2, CHCl$_3$)
3) Molecular weight: 300
4) molecular formula: $C_{20}H_{28}O_2$
5) $^1$H-NMR(CDCl$_3$, 300 MHz) δ 1.13(s, 3H, H-19), 1.21(s, 3H, H-20), 1.22 (d, J=4.23 Hz, 6H, 3H-16, 17), 1.28(m, 2H), 1.44(m, 3H), 1.79(m, 3H), 2.22(m, 1H), 2.79(m, 2H, H-7), 3.09(m, 1H, H-15), 4.52(s, 1H, C12-OH), 6.62(s, 1H, H-11), 6.82(s, 1H, H-14), 9.24(s, 1H, —CHO).

6) $^{13}$C-NMR(CDCl$_3$, 75 MHz) δ 14.0(C-19), 17.8(C-2), 21.5(C-6), 22.5(C-16), 22.7(C-17), 25.0(C-20), 26.8(C-15), 29.0(C-7), 32.0(C-3), 36.2(C-10), 37.8(C-1), 42.8(C-5), 49.8 (C-4), 110.8(C-11), 126.7(C-8), 126.9(C-14), 132.0(C-13), 147.2(C-9), 150.9(C-12), 206.4(C-18).

EXAMPLE 3

Extraction, Isolation and Purification of Terpenoid Compounds from *T. nucifera*

1. Extraction, Isolation and Purification of Compounds from *T. nucifera*

1 kg of *T. nucifera* leaves purchased in Jeju island, Korea, was washed and dried. The dried *T. nucifera* leaves were dipped in 4 l of 100% methanol, which was left at room temperature for 3 weeks. The solution was filtered with a filter paper, and charcoal (100 g) was added thereto, followed by stirring at room temperature for 12 hours. The solution was filtered and then concentrated under reduced pressure to give an oily yellow substances. The product was suspended in 200 ml of water, followed by filtering with a filter paper. The upper layer was dissolved in ethyl acetate, which was concentrated to give 40 g of oily yellow substances. The concentrated solution obtained above was dissolved in dichloromethane, to which n-hexane was added slowly, resulting in recrystalization. After filtering with a filter glass, the liquid phase was concentrated to give 30 g of the oily substances. The oily fractions obtained above have excellent hACAT-1 and hACAT-2 inhibiting activities.

Silica-gel column chromatography (Silica-gel: Merck, Art. 9385, Column size: φ7×40 cm) was performed with 16 g of the above oily fraction by using the mixed solvents of ethyl acetate and n-hexane as mobile phases. At this time, the mixed solvents used as mobile phases was developed by 1000 ml respectively as n-hexane:EtOAc=10:1, 5:1, 3:1, 1:1 and EtOAc 100% (v/v) to isolate 11 fractions (fraction 1~11).

Fraction 5 (6 g) showing high ACAT inhibiting activity was separated by silica-gel column chromatography (Column size: φ4×20 cm) by using the mixed solvent of n-hexane and ethyl acetate as a mobile phase. At this time, the mixed solvent used as a mobile phase was developed as n-hexane:EtOAc=7:1 (v/v) to isolate 7 fractions (fraction 5-1~5-7) (250 ml each). Fraction 5-4 (100 mg) showing excellent ACAT inhibiting activity was also separated by silica-gel column chromatography (Column size: φ2.5×10 cm). The solution was developed by using chloroform 100% as a mobile phase solvent, as a result, 4 fractions (fraction 5-4-1~5-4-4) were separated (50 ml each). And, a pure active compound of formula 2 was obtained (25 mg) from the fraction 5-4-1.

Silica-gel column chromatography (Column size: φ1.5×20 cm) was performed with fraction 10 (1.34 g) obtained from the first column by mobile phase solvent of methylenechloride:methanol=50:1 (v/v), resulting in the isolation of 14 fractions (fraction 10-1~10-14) (50 ml each). At this time, active fraction 10-4 (100 mg) was developed by using methanol:water=15:1 as a mobile phase solvent, followed by C18 reversed phase column chromatography (Column size: φ1.5×10 cm). As a result, 11 fractions (45 ml each) were isolated. Silica gel column chromatography (Column size: φ1×8 cm) was performed with the fraction 10-4-5 having strong inhibiting activity by using the mixed solvents of n-hexane and ethyl acetate as mobile phases. At this time, the mixed solvents were prepared at the ratios of n-hexane:EtOAc=50:1, 30:1, 10:1, 1:1 (v/v) and EtOAc 100%. As a result, 5 fractions (10-4-5-1~10-4-5-5) were separated (30 ml each). A pure active compound of formula 3 (76 mg) was obtained from the fraction 10-4-5-2.

A compound of formula 4 (40 mg) was obtained by using a recrystallizing solvent n-hexane:EtOAc=5:1 (v/v) from the fraction 11 (149 mg) obtained from the first column.

C18 reversed phase column chromatography (Column size: φ1.5×13 cm) was performed with fraction 10-6 (85 mg), which was comparatively active among 14 fractions obtained from the second column, by developing the mobile phase solvent of methanol:water=10:1 (v/v), resulting in the separation of 12 fractions (fraction 10-6-1~10-6-12) (45 ml each). Among those fractions, one of active fraction 10-6-3 (40 mg) was separated by silica-gel column chromatography (Column size: φ1×7 cm) by developing the mixed solvents of n-hexane:EtOAc=15:1, 10:1, 5:1, 1:1 (v/v) and EtOAc 100%. As a result, 5 fractions (10-6-3-1~10-6-3-5) were separated (30 ml each). And a pure active compound of formula 5 (15 mg) was obtained from the fraction 10-6-3-1.

2. Analyses of the Structures of Terpenoid Compounds

The structures of the compounds obtained in the above 1, was investigated. As a result, the compound of formula 2 was identified as isopimaric acid [Y.-H. Kuo and W.-C. Chen, *J. Chin. Chem. Soc.*, 46: 819, 1999], the compound of formula 3 was identified as dehydroabietinol [H. L. Ziegler et al., *Planta Med.*, 68: 547, 2002], the compound of formula 4 was identified as kayadiol [J. D. P. Teresa et al., *Argic. Biol. Chem.*, 35: 1068, 1971] and the compound of formula 5 was identified as δ-cadinol [*Bull. Chem. Soc. Jpn.*, 137: 1053, 1963].

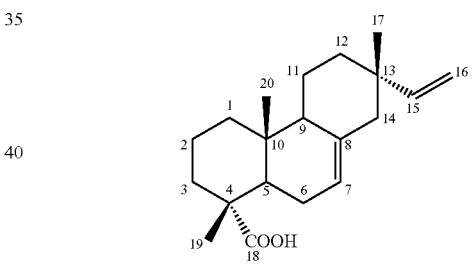

[Formula 2]: Isopimaric acid

1) Physical property: Coloress prizm, M.P. 185~187° C.
2) Polarity: $[\alpha]_D^{25}$+10.5° (c=0.42, EtOH)
3) Molecular weight: 302
4) Molecular formula: $C_{20}H_{30}O_2$
5) $^1$H-NMR(CDCl$_3$, 500 MHz) δ 0.86 (s, 3H, H-19), 0.91 (s, 3H, H-20), 1.12 (m, 1H), 1.27 (s, 3H, H-17), 1.37 (m, 2H), 1.48 (m, 1H), 1.55 (m, 3H), 1.67-2.03 (m, 9H), 4.87 (dd, J=1.7, 10.8 Hz, 1H, H-16ab, H-16ax), 4.93 (dd, J=0.6, 17.5 Hz, 1H, H-16ba, H-16bx), 5.32 (d like, J=4.1 Hz, 1H, H-7), 5.80 (dd, J=10.8, 17.6 Hz, H-15ax, H-15bx), 12.1 (brs, 1H, —COOH).
6) $^{13}$C-NMR(CDCl$_3$, 125 MHz) δ 15.3 (C-20), 17.1 (C-19), 17.9 (C-2), 20.0 (C-17), 25.2 (C-6), 35.0 (C-10), 36.1 (C-12), 36.8 (C-3), 37.0 (C-13), 38.8 (C-1), 45.0 (C-5), 46.1 (C-4), 46.3 (C-14), 52.0 (C-9), 109.3 (C-16), 121.0 (C-7), 135.7 (C-8), 150.3 (C-15), 185.6 (C-18).
7) EIMS(rel. int.) m/z [M]$^+$105 (40.7), 187 (36.9), 241 (47.8), 257 (30.9), 273 (26.9), 287 (47.1), 302 (100.0).

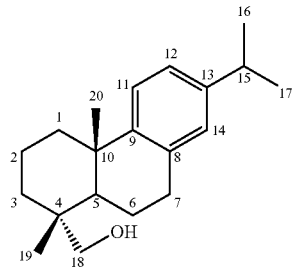

[Formula 3]: Dehydroabietinol

1) Physical property: Viscous oil
2) Polarity: $[\alpha]_D^{25}$ +50° (c=0.24, CHCl$_3$)
3) Molecular weight: 286
4) Molecular formula: $C_{20}H_{30}O$
5) $^1$H-NMR(CDCl$_3$, 300 MHz) δ 0.90 (s, 3H, H-19), 1.22 (s, 3H, H-20), 1.23 (t like, J=3.6 Hz, 6H, H-16, 17), 1.34-1.50 (m, 3H, H-1α, H-3), 1.63-1.82 (m, 5H, H-2, 5, 6), 2.29 (d like, J=12.6 Hz, 1H, H-1 ), 2.79-2.92 (m, 3H, H-7, 15), 3.24 (d, J=11.1 Hz, 1H, H-18α), 3.48 (d, J=11.1 Hz, 1H, H-18β), 6.89 (s, 1H, H-14), 6.99 (d, J=8.1 Hz, 1H, H-12), 7.19 (d, J=7.8 Hz, 1H, H-11).
6) $^{13}$C-NMR(CDCl$_3$, 75 MHz) δ 17.4 (C-19), 18.6 (C-2), 18.8 (C-6), 24.0 (C-16, 17), 25.3 (C-20), 30.1 (C-7), 33.4 (C-15), 35.1 (C-3), 37.3 (C-10), 37.8 (C-4), 38.4 (C-1), 43.9 (C-5), 72.2 (C-18), 123.8 (C-12), 124.2 (C-11), 126.8 (C-14), 134.7 (C-8), 145.5 (C-13), 147.3 (C-9).
7) EIMS(rel. int.) m/z [M]$^+$159 (47.5), 173 (60.9), 185 (27.0), 253 (100), 271 (87.2), 286 (32.6).

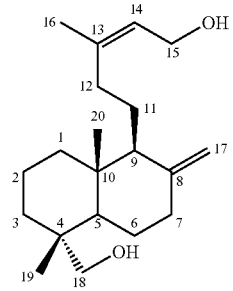

[Formula 4]: Kayadiol

1) Physical property: Amorphous powder
2) Polarity: $[\alpha]_D^{25}$ +18.4° (c=0.3, CHCl$_3$)
3) Molecular weight: 306
4) Molecular formula: $C_{20}H_{34}O_2$
5) $^1$H-NMR(CDCl$_3$, 500 MHz) δ 0.72 (s, 3H, H-20), 0.75 (s, 3H, H-18), 1.02 (dt, J=4.2, 12.7 Hz, 1H), 1.28 (m, 1H), 1.35 (dt, J=4.2, 12.7 Hz, 1H), 1.37-1.48 (m, 4H), 1.55-1.65 (m, 5H), 1.67 (s, 3H, H-16), 1.76-1.84 (m, 2H), 2.00 (dt, J=4.6, 12.6 Hz, 1H), 2.38 (m, 1H), 3.10 (d, J=10.9 Hz, 1H, H-19a), 3.42 (d, J=10.9 Hz, 1H, H-19b), 4.15 (d, J=6.7 Hz, 2H, H-15), 4.52 (s, 1H, H-17a), 4.84 (s, 1H, H-17b), 5.39 (t, J=6.6 Hz, 1H, H-14).
6) $^{13}$C-NMR(CDCl$_3$, 125 MHz) δ 15.0 (C-20), 16.4 (C-16), 17.6 (C-2), 18.7 (C-11), 21.8 (C-6), 24.2 (C-19), 35.4 (C-3), 38.0 (C-1), 38.1 (C-12), 38.4 (C-10), 38.6 (C-7), 39.5 (C-4), 48.5 (C-5), 56.2 (C-9), 59.4 (C-15), 72.0 (C-18), 105.5 (C-17), 123.1 (C-14), 140.5 (C-13), 148.3 (C-8).

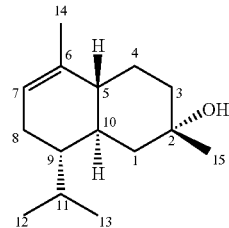

[Formula 5]: δ-cadinol

1) Physical property: White powder, M.P.=135.5~136° C.
2) Polarity: $[\alpha]_D^{25}$ −100° (c=0.24, CHCl$_3$)
3) Molecular weight: 222
4) Molecular weight: $C_{15}H_{26}O$
5) $^1$H-NMR(CDCl$_3$, 300 MHz) δ 0.79 (d, J=6.9 Hz, 3H, H-12 or H-13), 0.87 (d, J=6.6 Hz, 3H, H-13 or H-12), 1.09 (m, 1H), 1.28 (m, 1H), 1.27 (s, 3H, H-15), 1.41-1.60 (m, 6H), 1.63 (s, 3H, H-14), 1.85-2.01 (m, 5H), 5.51 (d like, J=4.2 Hz, 1H, H-7).
6) $^{13}$C-NMR(CDCl$_3$, 75 MHz) δ 15.3, 18.5, 21.5, 21.7, 23.6, 26.4, 27.9, 31.1, 35.3, 36.8, 44.1, 45.4, 72.5 (C-2), 124.6 (C-7), 134.3 (C-6).

EXPERIMENTAL EXAMPLE 1

Investigation of Anti-oxidative Activity of *T. nucifera* Extracts or Abietane Diterpenoid Compound Isolated from the Same of the Present Invention by TBARS Method In order to investigate anti-oxidative activity to LDL of *Torreya nucifera* extract or abietane diterpenoid compound isolated from the same, following experiments were performed.

$Cu^{2+}$ is known to mediate LDL-oxidation. Thus, in the present invention, dialdehyde, which is an oxidation product of unsaturated fatty acid formed during $Cu^{2+}$ mediated LDL-oxidation, was measured by thiobarbituric acid reactive substances (TBARS) method in order to investigate the LDL anti-oxidative activity of *T. nucifera* extracts or abietane diterpenoid compound separated from the same (Packer, L. Ed. (1994) *Methods in Enzymology* Vol. 234, Oxygen radicals in biological Systems Part D. Academic press, San Diego).

Centrifugation was performed with 300 ml of human blood plasma by using a ultracentrifuge at 100,000×g for 24 hours to remove floating VLDL/chylomicron layer in the upper part. The specific gravity of the remaining solution was adjusted to 1.063 g/ml. Centrifugation was performed again at 100,000×g for 24 hours, and 25 ml of the floating LDL (1.5~2.5 mg protein/ml) in the upper layer was separated.

20 μl of the separated LDL (protein concentration, 50-100 μg/ml) was mixed with 210 μl of 10 mM phosphate-buffered saline (PBS), to which 10 μl of *T. nucifera* extracts or abietane diterpenoid compound isolated from the same was added respectively.

*T. nucifera* extracts or abietane diterpenoid compound isolated from the same was dissolved in DMSO (dimethylsulfoxide), and the solution was diluted at different concentrations before use. Only a solvent was added to a negative control, while probucol was added to a positive control.

10 μl of 0.25 mM $CuSO_4$ was added to the solution, followed by further reaction at 37° C. for 4 hours. Then, the reaction was quenched by adding 1 ml of 20% trichloroacetic acid (TCA). 1 ml of 0.67% thiobarbituric acid (TBA) solution dissolved in 0.05 N NaOH solution was added to the solution, followed by stirring for 10 seconds. The solution was heated at 95° C. for 5 minutes to induce coloring, then cooled down in ice water. Centrifugation was performed at 3000 rpm for 5 minutes to separate supernatant. $OD_{540}$ was measured with a UV/VIS spectrophotometer. Malondialdehyde (MDA) detected by the above coloring was quantified.

PBS standard solution containing 0~10 nmol MDA was prepared by 250 µl with tetramethoxypropane malonaldehyde bis (dimethylacetal) storage solution.

Coloring was also induced in the standard solution in analogy to the procedure as described above and then $OD_{540}$ was measured to draw a standard curve of MDA.

MDA was quantified by using the standard curve in experiments with *T. nucifera* extracts or abietane diterpenoid compound isolated from the same.

The results are shown in Table 1.

TABLE 1

| Compound | | $IC_{50}(\mu M)$ |
|---|---|---|
| *T. nucifera* leaves | Hot water extracts (4 µg/ml) | 40% inhibition |
| | Methanol extracts (4 µg/ml) | 71% inhibition |
| *T. nucifera* seeds | Hot water extracts (4 µg/ml) | 35% inhibition |
| | Methanol extracts (4 µg/ml) | 52% inhibition |
| | R = methyl | 1.90 |
| | R = hydroxymethyl | 0.43 |
| | R = aldehyde | 0.92 |
| | R = methylester | 1.10 |
| | R = dimethoxymethyl | 1.80 |
| Probucol (Positive control) | | 1.55 |

As shown in Table 1, $IC_{50}$ value of *T. nucifera* extracts (hot water extracts and methanol extracts of leaves and seeds) of the present invention or abietane diterpenoid compounds isolated from the same was very low, indicating that the extracts has excellent anti-oxidative activity to LDL.

Therefore, *T. nucifera* extracts of the present invention or abietane diterpenoid compounds isolated from the same can be effectively used for the prevention and the treatment of cardiovascular diseases including hyperlipidemia and atherosclerosis which are caused by oxidation of LDL.

EXPERIMENTAL EXAMPLE 2

Effect on ACAT Activity of *T. nucifera* Extracts or Abietane Diterpenoid Compound or Terpenoid Compound Isolated from the Same of the Present Invention Following experiments were performed to investigate the effect on ACAT activity of *T. nucifera* extracts or abietane diterpenoid compound or terpenoid compound isolated from the same of the present invention.

1. Preparation of ACAT Enzyme Sources

In order to investigate the effect on hACAT-1 and hACAT-2 activities, hACAT-1 and hACAT-2 proteins were first obtained by taking advantage of baculovirus expression system.

cDNAs of hACAT-1 and hACAT-2 obtained from human liver cDNA library screening were inserted into baculovirus transfer vector, which was then introduced into insect sf9 cells to produce virus. Then, recombinant viruses of hACAT-1 and hACAT-2 were separated by plaque purification method, and amplification was performed three times to increase titer of viral stock. Hi5 insect cells having a good protein expression efficacy were infected with the recombinant virus, making multiplicity of infection as 1, followed by shaking culture at 27° C. for one day.

The cultured Hi5 cells over-expressing hACAT-1 and hACAT-2 were centrifuged at 500×g for 15 minutes to separate microsomal fraction. Then, cells were crushed in hypotonic buffer by quick freezing quick thawing, followed by ultracentrifugation at 100,000×g for one hour.

The obtained microsomal fractions were suspended in storage buffer solution, adjusting protein content to 8 mg/ml, which was stored in a deep freezer before using.

2. Measurement of ACAT Activity 6.67 µl of cholesterol dissolved in acetone at the concentration of 1 mg/ml was mixed with 6 µl of 10% triton WR-1339 (Sigma Co.) in acetone. And acetone was evaporated by nitrogen gas. Distilled water was added to the resultant mixture to adjust the content of cholesterol to 30 mg/ml.

To 10 µl of cholesterol solution was added 10 µl of 1 M $KH_2PO_4$ (pH 7.4), 5 µl of 0.6 mM BSA (bovine serum albumin), 10 µl of the microsomal solution obtained above, 10 µl of sample (*T. nucifera* extracts or abietane diterpenoid compound isolated from the same) and 45 µl of distilled water (total 90 µl). The mixture was pre-incubated in a 37° C. water bath for 30 minutes.

10 µ of [1-$^{14}$C]oleyl-CoA solution (0.05 µCi, final concentration: 10 µM) was added to the pre-incubated mixture, which was reacted in a 37° C. water bath for 30 minutes. To the mixture was added 500 µl of isopropanol:heptane solution (4:1 (v/v)), 300 µl of heptane and 200 µl of 0.1 M $KH_2PO_4$ (pH 7.4), which was stirred vigorously with vortex and then allowed to phase separation under gravity at room temperature for 2 minutes.

The 200 µl of upper phase was put in a scintillation vial, to which 4 ml of scintillation solution (Lipoluma, Lumac Co.) was added. Radioactivity of the upper phase was measured by a scintillation counter (1450 Microbeta liquid scintillation counter, Wallacoy, Finland).

ACAT activity was calculated based on the the radioactivity, the amount of synthesized cholesteryl oleate, measured above and expressed as a defined unit, pico mole per 1 mg of protein for 1 minute (pico mole/minute/mg protein).

The results are shown in Table 2.

TABLE 2

| Compound | | $IC_{50}(\mu M)$ | |
|---|---|---|---|
| | | hACAT-1 | hACAT-2 |
| *T. nucifera* leaves | Hot water extracts (100 µg/ml) | 65% inhibition | 59% inhibition |
| | Methanol extracts (100 µg/ml) | 81% inhibition | 77% inhibition |
| *T. nucifera* seeds | Hot water extracts (100 µg/ml) | 51% inhibition | 46% inhibition |
| | Methanol extracts | 41% | 45% |

TABLE 2-continued

| | | IC$_{50}$(μM) | |
|---|---|---|---|
| Compound | | hACAT-1 | hACAT-2 |
| | (100 μg/ml) | inhibition | inhibition |
| [structure] | R = methyl | 46 | 88 |
| | R = hydroxymethyl | 74 | 65 |
| | R = aldehyde | 37 | 42 |
| | R = methylester | 129 | 309 |
| | R = dimethoxymethyl | 98 | 199 |
| Formula 2 | Dehydroabietinol | 41 | 60 |
| Formula 3 | Isopimaric acid | 229 | 263 |
| Formula 4 | Kayadiol | 120 | 155 |
| Formula 5 | δ-cadinol | 79 | — |

As shown in Table 2, *T. nucifera* extracts (hot water extracts and methanol extracts of leaves and seeds) of the present invention or abietane diterpenoid compounds or terpenoid compounds isolated from the same have excellent hACAT-1 and hACAT-2 inhibiting activities.

Therefore, *T. nucifera* extracts or abietane diterpenoid compounds or terpenoid compounds isolated from the same of the present invention can be effectively used for the prevention and the treatment of cardiovascular diseases including hyperlipidemia and atherosclerosis caused by the synthesis and the accumulation of cholesteryl ester.

EXPERIMENTAL EXAMPLE 3

Cholesterol-lowering Effect by *T. nucifera* Extracts of the Present Invention

In order to investigate the blood cholesterol-lowering effect of *T. nucifera* extracts of the present invention, following experiments were performed.

30 specific pathogens free male C57BL/6J mice at the age of 6 weeks were raised in an animal facility, in which temperature was maintained as 22±3° C., humidity was kept as 55±10% and light was regulated as 12L/12D. The mice were adapted for about one week before being used for experiments. When they were at the age of 7 weeks (weight: 20~22 g), they were divided into 5 groups according to randomized block design. Group 1 mice were given with high-cholesterol/high-fat diet (CRF-1; AIN-76 test animal's normal diet supplemented with 1.25% cholesterol and 15% fat, Orient Yeast Co. Ltd., Japan), group 2 mice were given with high-fat/high-cholesterol (HFHC) diet together with 1% methanol extracts (wt/wt diet) of *T. nucifera* leaves (or 1% hot water extracts of *T. nucifera* leaves), and group 3 mice were treated with HFHC diet together with 0.1% probucol (wt/wt diet). All the mice of every group were free to take the diet and water for 10 days. Dietary intake was recorded everyday and weights of animals were measured every 5 days. Upon completion of breeding, all the records were analyzed. As a result, there was no significant difference in dietary intake and in weight gaining among three groups, suggesting the normal growth in those groups.

All the mice in three groups were sacrificed 10 days after the beginning of animal tests, then their blood was examined.

Blood was taken from retro-orbital sinus of the sacrified mice by heparin treated capillary tube. Centrifugation was performed with blood at 8,000×g for 10 minutes. Blood plasma was separated from supernatant and then stored in a deep freezer.

Total cholesterol content (TC) in blood plasma of each mouse of experimental group was measured by using a blood chemistry analyzer (CIBA Corning 550 Express, USA). In order to measure HDL-cholesterol, HDL measuring reagent (Chiron Diagnostics Co., USA), produced by the modified method for HDL measurement (references [①Stein E. A., et al.: Development and evaluation of a method for quantitation of plasma high-density-lipoprotein cholesterol. *Clin. Chem.* 24: 1112-1115, 1978; ② Finley P. R., et al.: Cholesterol in high-density lipoprotein: use of Mg$^{2+}$/dextran sulfate in its enzymatic measurement. *Clin. Chem.*, 24: 931-933, 1978; ③ Warnick G. R., et al. Dextran sulfate-Mg 2+ precipitation procedure for quantitation of high-density lipoprotein cholesterol. *Clin. Chem.* 28: 1379-1388, 1982]) in which dextran sulfate and magnesium sulfate were added to serum of each mouse to precipitate LDL and VLDL and then HDL in supernatant was measured, was mixed with blood plasma of each experimental group at the ratio of 1:10. The mixture was reacted in a 20~25° C. incubator for 5 minutes, followed by centrifugation at 8,000×g for 10 minutes. The resultant supernatant was put in a blood chemistry analyzer. A statistical computer program (Microsoft Excel, Version 7.0) was used to investigate and confirm (student t-test) the significance in difference in the results of blood analysis among experimental groups.

The contents of total cholesterol and HDL-cholesterol are shown in Table 3 and in Table 4.

TABLE 3

| | HFHC diet group | HFHC diet + methanol extracts of *T. nucifera* leaves group | HFHC diet + probucol group |
|---|---|---|---|
| Total cholesterol (mg/dl) | 207 ± 28.5 | 148.8 ± 28.5 | 177.0 ± 33.7 |
| HDL-cholesterol (mg/dl) | 54.1 ± 6.0 | 39.2 ± 6.0 | 41.7 ± 6.4 |
| HDL/total cholesterol (%) | 26.4 | 26.9 | 24.3 |

TABLE 4

| | HFHC diet group | HFHC diet + hot water extracts of *T. nucifera* leaves group | HFHC diet + probucol group |
|---|---|---|---|
| Total cholesterol (mg/dl) | 204.5 ± 33.5 | 180.6 ± 29.3 | 180.9 ± 32.6 |
| HDL-cholesterol (mg/dl) | 49.3 ± 6.6 | 43.7 ± 5.5 | 44.3 ± 6.5 |
| HDL/total cholesterol (%) | 24.1 | 24.2 | 24.5 |

As shown in Table 3, total cholesterol in plasma was 28.1% reduced in the group treated with methanol extracts of *T. nucifera* leaves, comparing to a control. In the meantime, total plasma cholesterol in a positive control treated with probucol was 14.5% reduced, comparing to a negative control.

As shown in Table 4, plasma cholesterol was 11.7% reduced in the group treated with hot water extracts of *T. nucifera* leaves, comparing to a control. The total cholesterol in a positive control treated with probucol was 11.5% reduced, comparing to a negative control.

The plasma HDL-cholesterol contents in *T. nucifera* extracts treating group and in a positive control group treated with probucol were not much different from that of a negative control, indicating that the extracts reduces the plasma LDL-cholesterol.

Therefore, *T. nucifera* extracts of the present invention can be effectively used for the prevention and the treatment of cardiovascular disease by lowering blood cholesterol and LDL-cholesterol as well.

EXPERIMENTAL EXAMPLE 4

Acute Toxicity Test in Mice Via Oral Administration

In order to investigate acute toxicity of *T. nucifera* extracts or abietane diterpenoid compound or terpenoid compound isolated from the same, following experiments were performed.

12 of each specific pathogens free female and male ICR mice at the age of 4 weeks (3 of each female and male/group) were raised in an animal facility where temperature was regulated to 22±3° C., humidity was adjusted to 55±10% and light was also regulated to 12L/12D. The animals were adapted for one week before being used. Feed for laboratory animals (CJ Corp., Korea, for mouse and rat) and drinking water were provided at any time after being sterilized.

*T. nucifera* extracts prepared in the above example or abietane diterpenoid compound or terpenoid compound isolated from the same was formulated by 50 mg/ml using 0.5% tween 80 as a solvent, then orally administered to mice at the concentration of 0.04 ml (100 mg/kg), 0.2 ml (500 mg/kg) and 0.4 ml (1,000 mg/kg) per 20 g of mouse body weight, respectively. Samples were administered orally just once. After the administration, side effects and death were observed for 7 days. Precisely, changes of any symptoms and death of an animal were observed 1 hour, 4 hours, 8 hours and 12 hours after the oral administration on the first day, and once or more in the morning and once or more in the afternoon from the second day through the 7$^{th}$ day.

On day 7, the animals were sacrificed and anatomized. The internal organs were examined by the naked eye. From the day of oral administration, weight changes were recorded everyday to investigate whether or not the weights of animals were decreased by *T. nucifera* extracts or abietane diterpenoid compound or terpenoid compound isolated from the same.

As a result, neither specific clinical symptoms nor death by the administration of the sample were observed in those animals. In addition, no toxicity was detected in mice either from the observation of weight changes, hematological tests, biochemical tests of blood, or autopsy.

Therefore, *T. nucifera* extracts, or abietane diterpenoid compounds or terpenoid compounds isolated from the same of the present invention are evaluated to be safe substance since it does not cause any toxic change in mice up to the level of 1,000 mg/kg and its estimated $LD_{50}$ value is much greater than 1,000 mg/kg in mice.

Preparative examples of the composition of the present invention are described hereinafter.

PREPARATIVE EXAMPLE 1

Preparation of Pharmaceutical Compositions

Pharmaceutical compositions including *T. nucifera* extracts, or abietane diterpenoid compound or terpenoid compound isolated from the same of the present invention were prepared.

| 1. Preparation of powders | |
|---|---|
| Abietane diterpenoid compound of formula 1 | 2 g |
| Lactose | 1 g |

The above-mentioned ingredients were mixed together, and airtight bag was filled with the mixture to prepare powders.

| 2. Preparation of tablets | |
|---|---|
| Abietane diterpenoid compound of formula 1 | 100 mg |
| Corn starch | 100 mg |
| Lactose | 100 mg |
| Magnesium stearate | 2 mg |

The above-mentioned ingredients were mixed together, and tablets were prepared by tabletting according to the conventional tablet producing method.

| 3. Preparation of capsules | |
|---|---|
| Abietane diterpenoid compound of formula 1 | 100 mg |
| Corn starch | 100 mg |
| Lactose | 100 mg |
| Magnesium stearate | 2 mg |

The above-mentioned ingredients were mixed together, and gelatin capsules were filled with the mixture to prepare capsules according to the conventional capsule producing method.

| 4. Preparation of injectable solutions | |
|---|---|
| Abietane diterpenoid compound of formula 1 | 10 μg/ml |
| Dilute hydrochloric acid BP | added to pH 3.5 |
| Injectable sodium chloride BP | Maximum 1 ml |

Abietane diterpenoid compound of formula 1 was dissolved in injectable sodium chloride BP, and pH of the solution was adjusted to 3.5 with diluted hydrochloric acid BP. The volume was also adjusted with injectable sodium chloride BP. After complete mixing, the solution filled 5 ml transparent glass type 1 ampules. By melting the glass, the solution was air-tight sealed, which was autoclaved at 120° C. for 15 minutes, resulting in the preparation of injectable solutions.

PREPARATIVE EXAMPLE 2

Preparation of Food

Food containing *T. nucifera* extracts, or abietane diterpenoid compound or terpenoid compound isolated from the same of the present invention was prepared as follows.

1. Preparation of Spices and Condiments

Spices and condiments for health improvement that contains abietane diterpenoid compound of formula 1 by 0.2~10 weight % were prepared.

2. Preparation of Tomato Ketchup and Source

Tomato ketchup and source for health improvement that contain abietane diterpenoid compound of formula 1 by 0.2~1.0 weight % were prepared.

3. Preparation of Flour Foods

Abietane diterpenoid compound of formula 1 was added to flour by 0.1~5.0 weight %, and the mixture was used to prepare bread, cake, cookies, cracker and noodles to produce health improving foods.

4. Preparation of Soups and Gravies

Health improving processed meat, noodle soups and gravies were prepared by adding abietane diterpenoid compound of formula 1 by 0.1~1.0 weight % to soups and gravies.

5. Preparation of Ground Beef

Health improving ground beef was prepared by adding abietane diterpenoid compound of formula 1 by 10 weight % to ground beef.

6. Preparation of Dairy Products

Abietane diterpenoid compound of formula 1 was added to milk by 0.1~1.0 weight %, which was then used for the production of health improving dairy products including butter and ice cream.

7. Preparation of Sun-Sik

Brown rice, barley, glutinous rice and Job's tears were gelatinized, dried and roasted by the conventional method, followed by pulverization with a pulverizer, resulting in 60-mesh granules.

Black bean, black sesame, *Perilla japonica* were steamed, dried and roasted by the conventional method, followed by pulverization with a pulverizer, resulting in 60-mesh granules.

Abietane diterpenoid compound of formula 1 was concentrated under reduced pressure in a vacuum concentrator, and then dried by spray dryer. The dried product was pulverized into 60-mesh granules.

Crops, seeds and the dried powder of abietane diterpenoid compound of formula 1 were mixed by the following ratio.

Crops (brown rice 30 weight %, job's tears 15 weight %, barley 20 weight %),

Seeds (*Perilla japonica* 7 weight %, black bean 8 weight %, black sesame 7 weight %), Dried powder of abietane diterpenoid compound of formula 1 (1 weight %),

*Ganoderma lucidum* (0.5 weight %),

*Rehmannia glutinosa* (0.5 weight %)

PREPARATIVE EXAMPLE 3

Preparation of Beverages

Beverages containing *T. nucifera* extracts, or abietane diterpenoid compound or terpenoid compound isolated from the same of the present invention were prepared.

1. Preparation of Carbonated Beverage

Sugar (5~10%), citric acid (0.05~0.3%), caramel (0.005~0.02%) and vitamin C (0.1~1%) were mixed together, to which purified water (79~94%) was added, resulting in syrup. The syrup was sterilized at 85~98° C. for 20~180 seconds, then mixed with cooling water at the ratio of 1:4. Carbon dioxide was injected by 0.5~0.82% thereto, resulting in the preparation of carbonated beverage containing abietane diterpenoid compound of formula 1.

2. Preparation of Health Beverage

Optional ingredients such as liquid fructose (0.5%), oligosaccharide (2%), sugar (2%), salt (0.5%), water (75%) and abietane diterpenoid compound of formula 1 were mixed homogeneously. After pasteurization, the mixture was put in a small container such as pet or glass bottle, resulting in the preparation of health beverage.

3. Preparation of Vegetable Juice 0.5 g of abietane diterpenoid compound of formula 1 was added to 1,000 ml of tomato or carrot juice to prepare health improving vegetable juice.

4. Preparation of Fruit Juice 0.1 g of abietane diterpenoid compound of formula 1 was added to 1,000 ml of apple or grape juice to prepare health improving fruit juice.

INDUSTRIAL APPLICABILITY

As explained hereinbefore, *T. nucifera* extracts, or abietane diterpenoid compound or terpenoid compound isolated from the same of the present invention has excellent anti-oxidative activity to LDL and inhibits ACAT activity effectively. In addition, *T. nucifera* extracts of the present invention reduce blood LDL cholesterol and total cholesterol.

Therefore, the composition of the present invention can be effectively used for the prevention and the treatment of cardiovascular diseases including hyperlipidemia and atherosclerosis caused by the LDL oxidation and the synthesis and accumulation of cholesteryl ester.

The invention claimed is:

1. An isolated, purified abietane diterpenoid compound represented by the following formula:

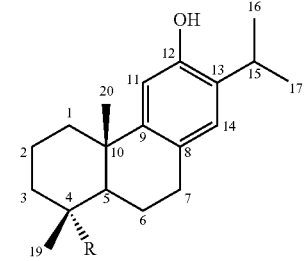

wherein R is dimethoxymethyl.

2. A composition for the treatment of cardiovascular disease comprising an isolated, purified compound represented by the following-formula:

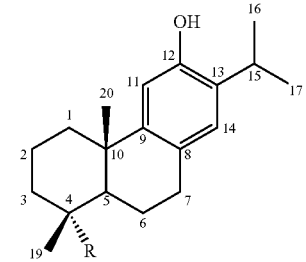

wherein R is dimethoxymethyl.

3. The composition according to claim 2, wherein the compound represented by formula 1 is prepared by extracting, isolating, and purifying from *Torreya nucifera*.

4. The composition according to claim 2, wherein the cardiovascular disease is hyperlipidemia or atherosclerosis.

* * * * *